(12) United States Patent
Nüsser et al.

(10) Patent No.: US 10,744,248 B2
(45) Date of Patent: Aug. 18, 2020

(54) CARDIAC ASSISTANCE SYSTEM HAVING TWO PUMPS

(71) Applicant: Berlin Heart GmbH, Berlin (DE)

(72) Inventors: Peter Nüsser, Kleinmachnow (DE); Nedim Arslan, Berlin (DE); Kurt Graichen, Berlin (DE); Jörg Müller, Berlin (DE)

(73) Assignee: BERLIN HEART GMBH, Berlin (DE)

( * ) Notice: Subject to any disclaimer, the term of this patent is extended or adjusted under 35 U.S.C. 154(b) by 178 days.

(21) Appl. No.: 15/951,652

(22) Filed: Apr. 12, 2018

(65) Prior Publication Data

US 2018/0228956 A1 Aug. 16, 2018

Related U.S. Application Data

(63) Continuation of application No. PCT/EP2016/074294, filed on Oct. 11, 2016.

(30) Foreign Application Priority Data

Oct. 12, 2015 (EP) .................................... 15189439

(51) Int. Cl.
*A61M 1/12* (2006.01)
*A61M 1/10* (2006.01)

(52) U.S. Cl.
CPC ............ *A61M 1/122* (2014.02); *A61M 1/101* (2013.01); *A61M 1/1008* (2014.02); *A61M 1/1031* (2014.02); *A61M 1/1086* (2013.01)

(58) Field of Classification Search
CPC .... A61M 1/12; A61M 1/1008; A61M 1/1031; A61M 1/101; A61M 1/1086
See application file for complete search history.

(56) References Cited

U.S. PATENT DOCUMENTS

| 8,226,712 B1* | 7/2012 | Frazier .................... A61F 2/064 623/3.13 |
| 8,376,927 B2 | 2/2013 | Tavor Lopez |
| 2003/0105420 A1 | 6/2003 | Hubbard et al. |

(Continued)

FOREIGN PATENT DOCUMENTS

| CN | 102046220 A | 5/2011 |
| DE | 10164942 | 4/2014 |

(Continued)

OTHER PUBLICATIONS

International Search Report with English translation, dated Jan. 9, 2017, pp. 1-3, issued in International Patent Application No. PCT/EP2016/074294, European Patent Office, Rijswijk, Netherlands.

*Primary Examiner* — Paula J Stice
(74) *Attorney, Agent, or Firm* — Brinks Gilson & Lione

(57) ABSTRACT

A cardiac assistance system is provided that comprises two pumps and cannulae connected thereto. A first pump of the two pumps is configured to connect to a right heart system via a first fluid channel. The first fluid channel formed at least partially by a first two cannulae of the cannulae. A second pump of the two pumps is configured to connect to a left heart system via a second fluid channel. The second fluid channel formed at least partially by a second two of the cannulae. The two pumps are configured as rotary pumps for arrangement outside a patient's body.

19 Claims, 2 Drawing Sheets

(56) References Cited

U.S. PATENT DOCUMENTS

| | | | |
|---|---|---|---|
| 2003/0163020 A1* | 8/2003 | Frazier | A61M 1/1015 600/16 |
| 2005/0209502 A1 | 9/2005 | Schmid et al. | |
| 2009/0264697 A1* | 10/2009 | Tovar Lopez | A61M 1/106 600/16 |
| 2012/0078031 A1 | 3/2012 | Burke et al. | |

FOREIGN PATENT DOCUMENTS

| | | |
|---|---|---|
| EP | 1481698 | 12/2004 |
| WO | WO 2014/165993 | 10/2014 |

\* cited by examiner

CARDIAC ASSISTANCE SYSTEM HAVING TWO PUMPS

CROSS-REFERENCE TO RELATED APPLICATIONS

This application is a continuation of International Application PCT/EP2016/074294, filed Oct. 11, 2016, which claims priority to European Patent Application No. 15189439.1 filed on Oct. 12, 2015. The entire contents of each of the above-identified applications are hereby incorporated by reference.

TECHNICAL FIELD

The present application is related to the field of mechanics and fluid mechanics and, in particular, to medical technology.

DETAILED DESCRIPTION

Figure 1:
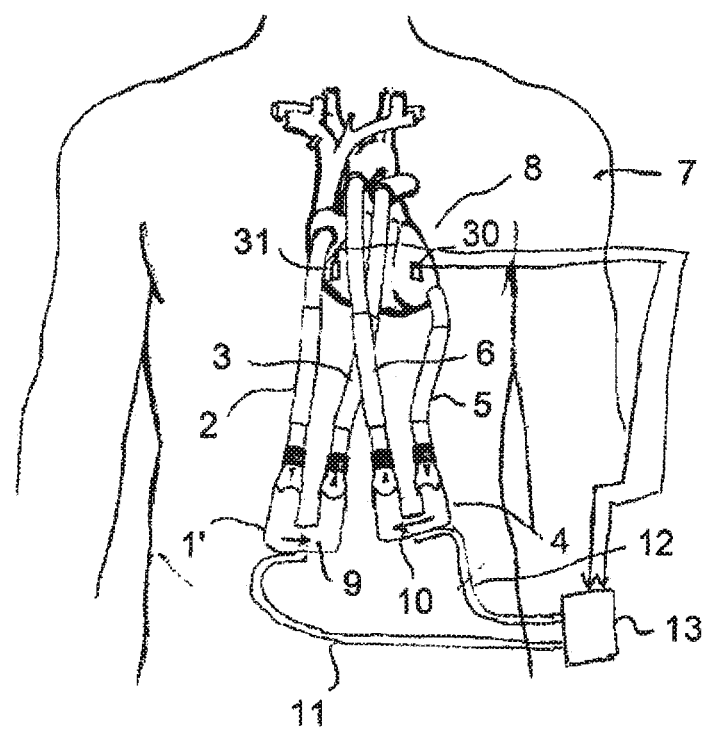
FIG. 1 schematically shows a patient's body with the patient's heart and two heart pumps.

For some time, cardiac assistance systems for patients have been known in which the ejection volume in one or both circulation loops of a patient's body is assisted by one or more cardiac assistance pumps. The function of the patient's heart can thus be assisted or replaced in part, moreover temporarily or in a lasting manner. In particular, assistance systems in which two pumps are arranged outside the patient's body and are connected by means of cannulae to various chambers of the heart on the one hand and blood vessels on the other hand are known in this field. In this way, both the left heart system and the right heart system can be assisted in a manner coordinated with one another. Pumps that are used for this purpose have previously often been known as diaphragm pumps with pneumatic drive which require a relatively high drive energy and provide pulsatile operation of the blood conveyance function.

However, the operation of cardiac assistance systems of this kind is bound to a continuous supply of power, which can be provided only either in a stationary manner, or requires the portability of power supplies in the form of relatively heavy and voluminous batteries/accumulators. Such systems often also require pneumatic units or other drive units in order to drive diaphragm pumps.

In addition, cardiac assistance systems having fully implanted, very small pumps, which are used temporarily or permanently for cardiac assistance are also known.

Against the background of the prior art, the object of the present invention is to create a cardiac assistance system having pumps which are arranged in a space-saving manner, operate with minimal power consumption, and convey blood within the body of the patient, even through relatively small cross-sections of fluid channels.

In order to solve the problem, a cardiac assistance system is provided, having two pumps and cannulae connected thereto, wherein a first pump is designed for connection to the right heart system, in particular to the right ventricle and the pulmonary artery, by means of a first fluid channel, formed at least partially by means of two cannulae, and the second pump is designed for connection to the left heart system, in particular to the left ventricle, on the one hand, and the aorta, on the other hand, by means of a second fluid channel, formed at least by means of two additional cannulae, wherein both pumps are formed as rotary pumps for arrangement outside a patient's body.

Due to the use of one or two rotary pumps for conveying blood, a relatively low energy consumption is provided, with a good controllability of the pressure and of the synchronised conveyed volume. For example, pumps with an axially conveying rotor or also pumps with a radially conveying rotor or a combination of both conveyance types can be used as rotary pumps.

Since, for the use of cannulae with fluid channels of small cross-section within the pumps, a relatively high pressure gradient should be produced, rotary pumps of this kind are operated for this purpose at high speeds. However, on the other hand, the speeds should not rise too much, so as to avoid blood damage as the blood is conveyed.

It can therefore be provided that a connector is provided in the course of at least one fluid channel connected to one of the pumps, in which connector the cross-section of the fluid channel reduces with increasing distance from the pump. As a result, the fluid channels have a relatively large cross-section in the region of the pumps, so that the blood in this region can be conveyed without too great a flow resistance. A constriction of the fluid channel cross-section is provided only for a part of the fluid channels, for example for the part of the fluid channels arranged within the patient's body. Cannulae of small cross-section can thus be used in this region which can also be easily implanted. A further benefit of this is in particular the use of a cardiac assistance system in children or babies.

Thus, a connector is required which produces a connection between a larger cross-section of the fluid channel in the region of one or both pumps and a smaller cross-section of the fluid channel in the region distanced from the pumps, for example within the patient's body. To this end, the cross-section of the fluid channel can be formed conically for example within the connector.

The connector itself can consist for example of a rigid material, in particular a plastic or metal, for example titanium. However, it can also consist of an elastomer material, such as a silicone elastomer.

A connector of this kind usually connects a first cannula having a larger inner and outer diameter to a second cannula, the inner and outer diameter of which are smaller than those of the first cannula. Here, the first cannula is closer to the heart pump than the second cannula.

In order to connect the connector in a fluid-tight manner either to a cannula connected to a pump or directly to a pump port in the region of the pump inlet or pump outlet, a connection element that consists of an elastomer is provided, for example. A connection element of this kind can be an annular sleeve, which is provided at each of its ends with snap rings, which can be snapped onto a cannula or a pump port on the one hand and on the other hand onto an end of the connector. The diameters of the connector, of the pump ports, and of the cannulae and of the connection element are advantageously coordinated with one another in such a way that the connection element can be clamped resiliently onto the other ports. A fluid-tight seal is thus achieved in the connection region.

The connector can additionally have an edge or groove via which a snap ring of the connection element is clamped on in such a way that a radially inwardly protruding rib of the connection element engages in the groove or behind the rib of the connector. The reliability of the fluid-tight seal is hereby improved further still. A similar rib/groove connection can also be provided in the connection region between the connection element and a pump port or a cannula.

It can additionally be provided that at least one of the pumps is connected to a graft. The cannula connected to an outlet of the blood pump is preferably connected to a graft at its end remote from the blood pump. By means of a graft of this kind, the cannula in question can be directly connected to a blood vessel by means of sutures.

It can additionally be provided that the cannulae each have a region designed for passage through the skin of the patient. All cannulae of the cardiac assistance system preferably can be guided or are guided through the skin of the patient. One cannula or both cannulae, which in each case connect a pump and the patient's heart to one another, can be roughened in portions in their outer region for example, so as to encourage ingrowth in the patient's skin in the region of the passage of the cannula through the skin. Instead of a roughening, a coating with a material that promotes growth into the skin can also be provided.

The produced pressure gradient of both pumps and the conveyed quantities can be selectively coordinated with one another. To this end, it is expedient however to control both pumps by means of a common control unit.

Furthermore, it is expedient to provide one or two or also more pressure sensors to which the control unit is connected. Here, at least one of the pressure sensors can be arranged in each case in one of the fluid channels or in a heart ventricle, so that the fluid channels each connected to one of the pumps respectively can be individually monitored in respect of the pressure and the conveyed volume and the pumps associated therewith can be suitably controlled.

As already mentioned above, it can also be provided that at least one connector is arranged directly at a pump inlet or outlet.

In the previous embodiments, it was always assumed that the cardiac assistance system has two rotary pumps. A further cardiac assistance system in accordance with this description is a cardiac assistance system with a pump and with cannulae connected thereto, wherein the pump is designed for connection to the right heart system, in particular to the right ventricle and the pulmonary artery, by means of a first fluid channel, formed at least partially by means of at least one cannula, or is designed for connection to the left heart system, in particular to the left ventricle, on the one hand, and the aorta, on the other hand, by means of a second fluid channel, formed at least partially by means of at least one cannula, characterised in that the pump is formed as a rotary pump for arrangement outside a patient's body.

Apart from a cardiac assistance system, a computer program product comprising a program for operating the control unit in such a way that the pressure and/or the volume flows in the two fluid channels connected one to each of the pumps respectively are coordinated with one another is also proposed.

Here, it can be provided in one embodiment that the pressure within the pumps or the pressure within the cannulae is adjusted to the physiological requirements of the heart system in question, for example the left or right heart system. If the cardiac assistance system comprises two blood pumps, both therefore convey the same volume flow within the same short period of time.

A program of this kind can control a method for operating a cardiac assistance system such that the performances of both pumps are controlled in such a way that the pressure and/or the volume flows in both fluid channels connected one to each of the pumps respectively are coordinated with one another.

By means of a suitable periodically fluctuating control of the pumps, a pulsatile conveying characteristic of the pumps can also be provided, which comes closer to the natural conveying characteristic of a healthy heart than a relatively constant, less pulsatile fluid flow through the blood vessels.

Figure 2:
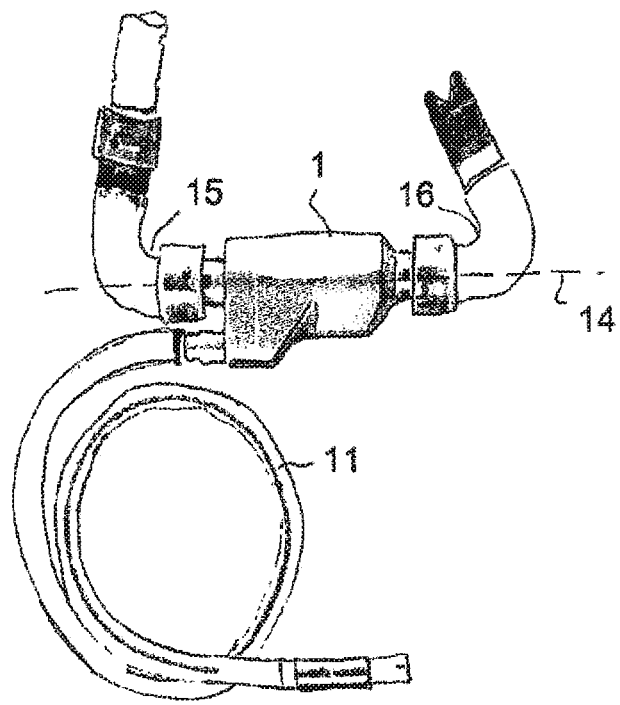
FIG. 2 shows an external view of a heart pump.
Figure 3:
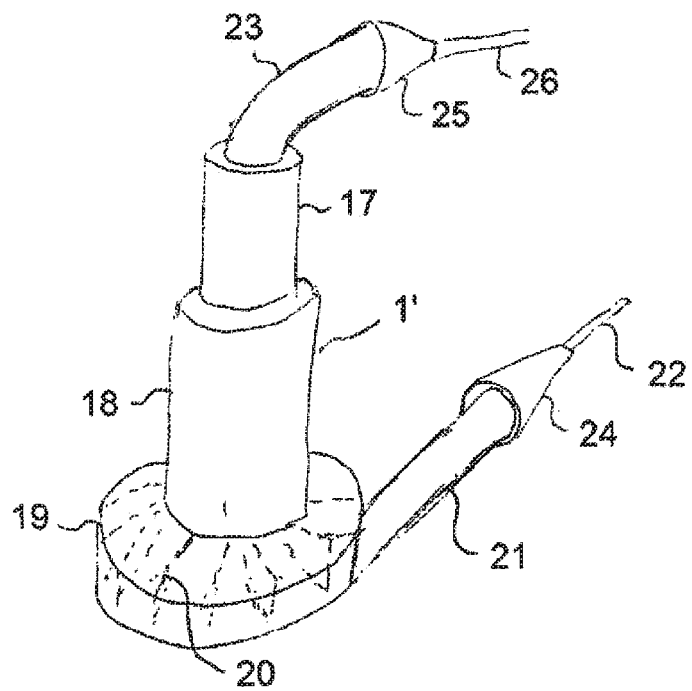
FIG. 3 shows a three-dimensional view of a further heart pump with a radially conveying rotor.
Figure 4:
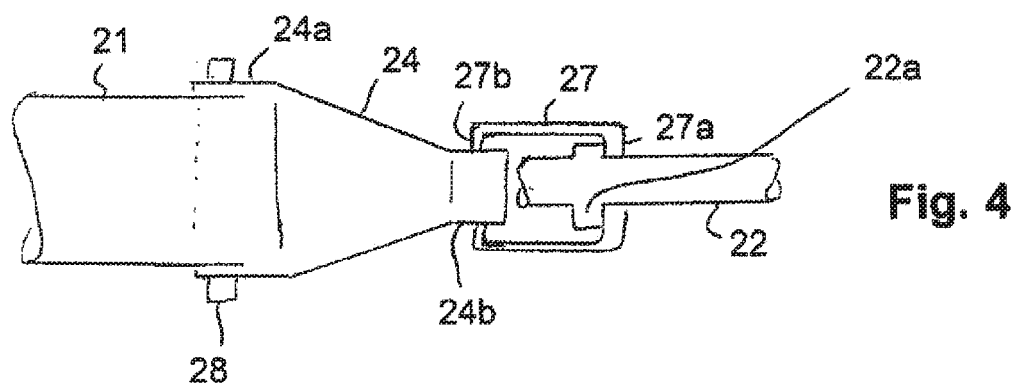
FIG. 4 shows a conical connector with connection elements.
Figure 5:
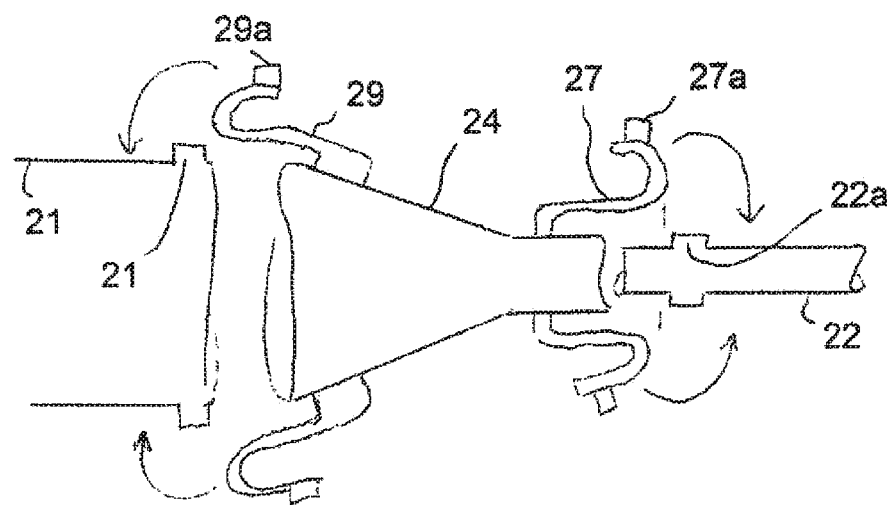
FIG. 5 shows a conical connector with connection elements, which comprise snap rings.

The presented cardiac assistance system and method for operation thereof will be detailed and explained hereinafter on the basis of exemplary embodiments with the aid of the accompanying figures of a drawing, in which:

FIG. 1 schematically shows a patient's body with the patient's heart and two heart pumps, FIG. 2 shows an external view of a heart pump, FIG. 3 shows a three-dimensional view of a further heart pump with a radially conveying rotor, FIG. 4 shows a conical connector with connection elements, and FIG. 5 shows a conical connector with connection elements which comprise snap rings.

FIG. 1 schematically shows the body 7 of a patient with the patient's heart 8. Two heart pumps 1, 4 are connected to the heart 8 by means of cannulae 2, 3, 5, 6. Here, the cannula 2 runs from the right atrium to the pump 1, whereas the cannula 3 runs from the pump 1 to the pulmonary artery. The cannula 5 leads from the apex to the second pump 4, and the cannula 6 leads from the pump 4 to the ascending aorta.

On the whole, the system constitutes a biventricular assistance system. The two pumps 1, 4 are formed as rotary pumps, each having a rotor that is driven by means of an electric motor and conveys blood in the axial direction by rotation at high speed. The rotation axes of the two rotors lie parallel to the arrows 9, 10 shown in FIG. 1, which each indicate the direction of blood flow during operation of the pump. Two cables 11, 12 are shown, which are used to guide through electrical leads from the electric motors driving the pumps 1, 4 to a common control unit 13.

The pumps 1, 4 can be operated in a manner coordinated with one another, wherein periodic fluctuations of the conveying capacity can be provided in order to imitate a pulsatile organic heart function. Within the various chambers of the heart 8 or in the cannulae 2, 3, 5, 6, flow rate sensors and/or pressure sensors can be provided in order to be able to coordinate with one another the conveying capacity and the pressure gradient across the two pumps 1, 4.

The sensor data are collected and processed in the control unit 13 and as appropriate are converted into control data for the pumps 1, 4 under consideration of captured physiological data of the patient. The control unit 13 for this purpose comprises at least one microcontroller, which is provided with a memory unit and is operated by means of a computer program. The programming of the control unit 13 and/or the parameterisation of the control of the pumps 1, 4 are/is possible individually and can be tailored to the patient.

FIG. 2 shows an example of a rotary pump as is provided in the cardiac assistance system of FIG. 1. The pump 1 has a housing, in which a rotor rotates about the rotation axis denoted in FIG. 2 by 14. An electrical lead is guided by the cable 11 to the pump 1. There, a magnetic field is generated by means of the electrical lead via an energised stator, which drives an inner rotor in a brushless manner. For example, the rotor can be supported with little friction both in the radial and axial direction by means of magnetic bearings.

Cannulae of relatively large cross-section are connected to the pump 1: one at the pump inlet 15 and one at the pump outlet 16. It can be expedient or necessary for cannulae of smaller cross-section on average to be connected to these cannulae of large dimensions, said smaller cannulae leading to the patient's heart and passing through the patient's skin. Since the pumps 1, 4 are arranged in numerous exemplary embodiments outside the patient's body, the patient's body is not compromised by cannulae of large dimensions in the region of the pumps. However, connectors are necessary which enable the transition from a large cannula diameter to a small cannula diameter.

FIG. 3 shows a three-dimensional view of a pump 1', which is formed as a radial pump. This means that the liquid is conveyed via a pump inlet 17 and an axial inflow region 18 to a rotor, which is arranged in the rotor housing 19 and is illustrated in a dashed manner, wherein the liquid is conveyed centrifugally in the radial direction by the rotor 20 and is transported via a pump outlet 21 to a cannula 22. The diameter of the pump outlet 21 is of such a size that the liquid can be conveyed in an unbraked manner to the greatest possible extent. The pump 1' is arranged outside the patient's body, jointly with the pump outlets and the shown cannulae 21 at the pump outlet and 23 at the pump inlet.

Connectors 24, 25 are provided, which reduce the fluid channel, in each case starting from a region lying closer to the pump 1' to a region lying further away from the pump 1'. Finer cannulae 22, 26 of reduced diameter compared to the cannulae 21, 23 are connected in a fluid-tight manner to the ends of the connectors 24, 25 remote from the pump. These cannulae 22, 26 of smaller diameter (both inner diameter and outer diameter) lead through the skin of the patient into the patient's body and as appropriate to the patient's heart or the large blood vessels.

Regions that are particularly suitable for passage through the skin of the patient, for example by means of a roughening at the surface or by application of an ingrowth layer, which particularly facilitates the growth of organic tissue, can be provided on the surface of the cannulae 22, 26.

The connectors 24, 25 are conical and cylindrically symmetrical in terms of their outer appearance and also in respect of their interior, so as to ensure the diameter reduction of the fluid channel in the most efficient way possible.

The connectors 24, 25 are connected in a fluid-tight manner to the cannulae 21, 23, 22, 26 by means of connection elements, which are not shown in greater detail in FIG. 3.

The reduction of the fluid channel/the fluid channels during the course of the diameter reduction in the connectors 24, 25 and the further course of the fine cannulae 22, 26 involves an increase of the flow resistance of the liquid to be conveyed, which must be compensated for additionally by the pump 1 or 1'.

In order to reduce the fluid resistance to the greatest possible extent, the length of the cannulae 21, 23, which in diameter are not much smaller than the pump inlets and outlets, can be optimised to such an extent that they practically lead as far as the patient's body, whereupon a connector 24, 25 is then connected in each case, followed by the fine cannulae 22, 26, wherein the passage through the skin of the patient lies in the starting region of the fine cannulae 22, 26 on the pump side, so that only a few centimetres of the cannulae 22, 26, in particular less than 10% of the total length of these cannulae, protrudes from the patient's body. The performance of the pumps required to generate the necessary pressure gradient and thus also the rotational speed during use of rotary pumps are thus reduced to the greatest possible extent. Blood damage, which can be more likely at high pump speeds, can thus be avoided.

The type of connection of the connectors 24, 25 to the cannulae 21, 23, 22, 26 will be explained in greater detail with reference to FIG. 4. In FIG. 3 the connector 24 is shown centrally between a cannula 21 of larger diameter and a second cannula 22 of smaller diameter. The cannula 22 arranged at the end of the connector 24 remote from the pump has a smaller diameter, both in respect of the outer diameter and the inner diameter, than the cannula 21 at the end of the connector 24 close to the pump.

The cannulae 21, 22 can be produced from a flexible plastic/elastomer, for example a silicone elastomer, or for example from polyethylene. The connector 24 usually also consists of a plastic, which can be more rigid however than the plastic from which the cannulae and/or the connection elements consist.

The connector 24 has cylindrical extension pieces 24a, 24b at each of its two ends, with the connection elements 27, 28 abutting said extension pieces. Here, in the shown example, the connection element 28 is formed simply as a clamping ring, which is thrown over the extension piece 24a and is clamped there, so that the extension piece 24a is clamped in a fluid-tight manner onto the outer diameter of the cannula 21. The connection can also be established in such a way that the cannula is drawn externally onto the extension piece 24a, which is expedient when the material of the cannula 21 is softer than the material of the connector 24. The clamping ring 28 can then be clamped over the outer diameter of the cannula 21.

A connection element 27 in the form of a tube piece with two radially inwardly pointing flanges 27a, 27b is shown in the region of the connector 24 remote from the pump. The cannula 22 can be slid into the extension 24b or into a position sitting externally on the extension 24. However, the connection element 27 can also be formed as a sleeve, which produces the connection between the connector 24 and the cannula 22, which are distanced from one another. However, it must then be ensured that there are no dead water spaces in the connection element 24. A direct connection between the connector and the cannula 22 is therefore advantageous.

The flange 27b of the connection element 27 can be resiliently clamped in a sealing manner onto the extension piece 24. For connection to a cannula 22, the connection element 27 can be resiliently widened, more specifically until the flange 27a is bent back towards the rear over the cylindrical part of the connection element 27. A position of this kind is shown in greater detail in FIG. 5. If the connection element 27 then snaps onto the cannula 22, the flange 27a contracts resiliently and clamps onto the cylindrical outer surface of the cannula 22. For improved solidarity and a reliable seal, the cannula 22 can have a peripheral rib 22a, behind which the flange 27a can sit.

The connection process is shown by way of example in FIG. 5, in which the connector 24 is firstly fitted together with the cannula 21 and the cannula 22, wherein the connection elements 27, 29 are both formed as snap ring connectors that can be bent back. This means that the shown position of the connection elements 27, 29 is stable until the free ends of the connection elements 27, 29 with the flanges 27a, 29a are actuated at the time of production of the connection, for example by a member of medical staff, in such a way that the connectors snap into place behind the ribs 22a of the cannula 22 and 21a of the cannula 21 so as to thus seal the fluid channel leading from the cannula 21 via the connector 24 to the cannula 22. In this way, a connection can be produced in a simple manner for example during the implantation process.

The proposed cardiac assistance system allows the use outside the patient's body of rotor pumps in conjunction with a tapering cross-section of the connecting fluid channels, even if cannulae having a small inner diameter are used within the patient's body, for example as in the case of babies.

Sensors 30, 31 for measuring the pressure can be provided in the heart chambers and are connected to the control unit 13 in order to control the pumps 1, 4 in a coordinated manner.

The control unit 13 may include a processor and/or a memory. The processor may be in communication with the memory. Examples of the processor may include a general processor, a central processing unit, a microcontroller, an application specific integrated circuit (ASIC), a digital signal processor, a field programmable gate array (FPGA), and/or a digital circuit, analog circuit, or some combination thereof.

The processor may be one or more devices operable to execute logic. The logic may include computer executable instructions or computer code stored in the memory or in other memory that when executed by the processor, cause the processor to perform the features implemented by the logic of control unit 13 and/or the cardiac assistance system. The computer code may include instructions executable with the processor.

The memory may be any device for storing and retrieving data or any combination thereof. The memory may include non-volatile and/or volatile memory, such as a random access memory (RAM), a read-only memory (ROM), an erasable programmable read-only memory (EPROM), or flash memory. Alternatively or in addition, the memory may include any other form of data storage device.

The control unit 13 may be implemented in many different ways. For example, the control unit 13 may include a circuit or circuitry. Each circuit or circuitry may be hardware or a combination of hardware and software. For example, each circuit or circuitry may include an application specific integrated circuit (ASIC), a Field Programmable Gate Array (FPGA), a digital logic circuit, an analog circuit, a combination of discrete circuits, gates, or any other type of hardware or combination thereof. Alternatively or in addition, each circuitry may include memory hardware, such as a portion of the memory, for example, that comprises instructions executable with the processor or other processor to implement one or more of the features of the circuitry. When any one of the circuitry includes the portion of the memory that comprises instructions executable with the processor, the circuitry may or may not include the processor. In some examples, each circuitry may just be the portion of the memory or other physical memory that comprises instructions executable with the processor or other processor to implement the features of the corresponding circuitry without the circuitry including any other hardware. Because each circuitry includes at least some hardware even when the included hardware comprises software, each circuitry may be interchangeably referred to as a hardware.

Some logic may be stored in a computer readable storage medium (for example, as logic implemented as computer executable instructions or as data structures in memory). All or part of the cardiac assistance system and its logic and data structures may be stored on, distributed across, or read from one or more types of computer readable storage media. Examples of the computer readable storage medium may include a flash drive, a cache, volatile memory, non-volatile memory, RAM, flash memory, or any other type of computer readable storage medium or storage media. The computer readable storage medium may include any type of nontransitory computer readable medium, such as a volatile memory, a non-volatile memory, ROM, RAM, or any other suitable storage device.

The processing capability of the cardiac assistance system may be distributed among multiple entities, such as among multiple processors and memories, optionally including multiple distributed processing systems. Parameters, databases, and other data structures may be separately stored and managed, may be incorporated into a single memory or database, may be logically and physically organized in many different ways, and may implemented with different types of data structures such as linked lists, hash tables, or implicit storage mechanisms. Logic, such as programs or circuitry, may be combined or split among multiple programs, distributed across several memories and processors, and may be implemented in a library, such as a shared library (for example, a dynamic link library (DLL)).

All of the discussion, regardless of the particular implementation described, is illustrative in nature, rather than limiting. For example, although selected aspects, features, or components of the implementations may be stored in memory(s), all or part of cardiac assistance system or systems may be stored on, distributed across, or read from other computer readable storage media.

The respective logic, software or instructions for implementing the processes, methods and/or techniques discussed above may be provided on computer readable storage media. The functions, acts or tasks illustrated in the figures or described herein may be executed in response to one or more sets of logic or instructions stored in or on computer readable media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one example, the instructions are stored on a removable media device for reading by local or remote systems. In yet other examples, the logic or instructions are stored within a given computer, central processing unit ("CPU"), graphics processing unit ("GPU"), or system.

Furthermore, although specific components are described above, methods, systems, and articles of manufacture described herein may include additional, fewer, or different components. For example, a processor may be implemented as a microprocessor, microcontroller, application specific integrated circuit (ASIC), discrete logic, or a combination of other type of circuits or logic. Similarly, memories may be DRAM, SRAM, Flash or any other type of memory. Flags, data, databases, tables, entities, and other data structures may be separately stored and managed, may be incorporated into a single memory or database, may be distributed, or may be logically and physically organized in many different ways. The components may operate independently or be part of a same apparatus executing a same program or different programs. The components may be resident on separate hardware, such as separate removable circuit boards, or share common hardware, such as a same memory and processor for implementing instructions from the memory. Programs may be parts of a single program, separate programs, or distributed across several memories and processors.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations.

The invention claimed is:

1. A cardiac assistance system comprising:
   two pumps and cannulae connected thereto, wherein a first pump of the two pumps is configured to connect to a right heart system via a first fluid channel, the first fluid channel formed at least partially by a first two cannulae of the cannulae, and wherein a second pump of the two pumps is configured to connect to a left heart system via a second fluid channel, the second fluid channel formed at least partially by a second two of the cannulae, wherein at least one of the cannulae includes a region configured to pass through skin, and wherein the two pumps are configured as rotary pumps, and the two pumps are further configured to operate outside a patient's body.

2. The cardiac assistance system according to claim 1, wherein a connector is fluidly coupled to at least one fluid channel connected to one of the two pumps, wherein a cross-section of the fluid channel reduces with increasing distance from the one of the two pumps.

3. The cardiac assistance system according to claim 2, wherein at least one connector is arranged directly at a pump inlet or a pump outlet.

4. The cardiac assistance system according to claim 2 wherein the connector is configured to connect, in a fluid-tight manner, to a cannula with a connection element comprising an elastomer.

5. The cardiac assistance system according to claim 2, wherein the cross-section of the fluid channel is conical.

6. The cardiac assistance system according to claim 2, wherein the connector comprises a rigid material.

7. The cardiac assistance system according to claim 6, wherein the rigid material comprises at least one of a plastic or a metal.

8. The cardiac assistance system according to claim 2, wherein the connector comprising an elastomer material.

9. The cardiac assistance system according to claim 1 wherein each of the cannulae have a region that is configured to pass through skin.

10. The cardiac assistance system according to claim 1, wherein the two pumps are connected to a common control unit.

11. The cardiac assistance system according to claim 10, wherein the common control unit is configured to control, by coordinated operation the two pumps, at least one of respective pressures or respective volume flows in the first fluid channel and the second fluid channel.

12. The cardiac assistance system according to claim 10, further comprising at least one pressure sensor to which the common control unit is connected.

13. The cardiac assistance system according to claim 12, wherein the at least one pressure sensor is arranged in one of the fluid channels or in a heart ventricle.

14. The cardiac assistance system according to claim 10 further comprising a first pressure sensor in communication with the common control unit and a second pressure sensor in communication with the common control unit, wherein the first pressure sensor is located in one of the fluid channels and a second pressure sensor is located in a heart ventricle.

15. The cardiac assistance system according to claim 1, wherein the right heart system includes a right ventricle and a pulmonary artery, wherein the left heart system includes a left ventricle and an aorta.

16. A method for operating a cardiac assistance system comprising:
   arranging a first pump and a second pump outside a patient's body;
   controlling operation of the first pump connected to a right heart system of the patient's body via a first fluid channel formed at least partially by a first two of a plurality of cannulae, wherein at least one of the cannulae includes a region configured to pass through skin;
   controlling operation of the second pump connected to a left heart system of the patient's body via a second fluid channel formed at least partially by a second two of the cannulae; and
   coordinating, based on controlled operation of the first pump or the second pump, at least one of respective pressures or respective volume flow in the first fluid channel and the second fluid channel.

17. The method according to claim 16, wherein the operation of the first pump and operation of the second pump is controlled in a pulsatile manner.

18. A cardiac assistance system comprising:
   at least one extra-corporeal pump and a plurality of cannulae connected thereto, wherein the at least one extra-corporeal pump is configured to connect to a right heart system via a first fluid channel formed at least partially by at least a first one of the cannulae or to a left heart system via a second fluid channel formed at least partially by at least a second one of the cannulae, wherein the at least one extra-corporeal pump is formed as a rotary pump configured to operate outside a patient's body, and wherein one or more of the cannulae includes a region configured to pass through skin.

19. The cardiac assistance system of claim 18 wherein the at least one extra-corporeal pump comprises a first pump configured to connect to the right heart system via the first fluid channel, the at least one extra-corporeal pump further comprising a second pump configured to connect to the left heart system via the second fluid channel.

* * * * *